(12) United States Patent
Hong

(10) Patent No.: US 8,574,922 B2
(45) Date of Patent: Nov. 5, 2013

(54) TARGETED CELL SEPARATION AND ENUMERATION DEVICE AND THE USE THEREOF

(76) Inventor: Bin Hong, Rockville, MD (US)

( * ) Notice: Subject to any disclaimer, the term of this patent is extended or adjusted under 35 U.S.C. 154(b) by 385 days.

(21) Appl. No.: 12/719,034

(22) Filed: Mar. 8, 2010

(65) Prior Publication Data

US 2011/0217729 A1 Sep. 8, 2011

(51) Int. Cl.
*C12Q 1/04* (2006.01)
*C12M 1/34* (2006.01)

(52) U.S. Cl.
USPC .............................. 436/172; 436/164

(58) Field of Classification Search
USPC ................................. 436/172, 164
See application file for complete search history.

(56) References Cited

U.S. PATENT DOCUMENTS

| | | | |
|---|---|---|---|
| 5,417,650 A * | 5/1995 | Gordon | 604/5.04 |
| 2005/0130294 A1 * | 6/2005 | Randall et al. | 435/287.2 |
| 2008/0318324 A1 * | 12/2008 | Chiu et al. | 436/64 |
| 2009/0035792 A1 * | 2/2009 | Singh et al. | 435/7.23 |
| 2010/0240142 A1 * | 9/2010 | Saiki et al. | 436/164 |

FOREIGN PATENT DOCUMENTS

JP 2009-115670 * 5/2009 .............. G01N 21/00

OTHER PUBLICATIONS

Brooks P. et al., Requirement of Vascular Integrin alpha v beta 3 for Angiogenesis, Science, Apr. 22, 1994, vol. 264, p. 569-571.*

* cited by examiner

*Primary Examiner* — Christine T Mui
(74) *Attorney, Agent, or Firm* — Trojan Law Offices

(57) ABSTRACT

This disclosure describes a portable device that conveniently applies cancer patient blood sample into a test strip to determine the level of the patient's metastatic circulating tumor cells. Proper use of this device provides end users with the diagnostic and prognostic information of the cancer patient, and any effect of applied therapies. The device can also be used to screen effective drugs for any known metastatic phenotype disruption.

9 Claims, 7 Drawing Sheets

TARGETED CELL SEPARATION AND ENUMERATION DEVICE AND THE USE THEREOF

FIELD OF INVENTION

This invention is related to a device that provides one stop shop for targeted cell separation and enumeration, and its use in cancer diagnosis, prognosis or drug discovery. More specifically the device is to facilitate point of care in vitro diagnosis for end users.

BACKGROUND

Cancer is the second most common cause of death in the US, accounting for nearly 1 of every 4 deaths. In 2009, more than 1,500 people died of cancer each day, claiming approximately 562,340 deaths of Americans entirely. The National Institutes of Health estimates overall costs of cancer in 2008 at $228.1 billion with $93.2 billion for direct medical costs (total of all health expenditures), $18.8 billion for indirect morbidity costs (cost of lost productivity due to illness), and $116.1 billion for indirect mortality costs (cost of lost productivity due to premature death).

Conventional cancer therapy has been focused on non-specific cytotoxic and/or radiation therapy, based on the observation that malignant cells divide at a more rapid rate than the normal cells. For example, ionizing radiation induces DNA damage that, upon multiple cell divisions, may lead to errors in transcription and translation resulting in cell death. Similarly, cytotoxic chemotherapy may interrupt microtubule formation that is essential for mitotic events, and ultimately affect cell survival. The conventional therapies have resulted in significant survival advantages in breast and colon cancer patients.

Despite the above noticed benefits, conventional therapies directed against rapidly dividing cells may also result in the death of epithelium (such as the lining of the gastrointestinal tract) or affect hematopoietic progenitors, resulting in cytopenia. These side effects not only reduce the quality of life of cancer patients, but also limit the dosage available for therapy, ultimately resulting therapeutic antitumor activity.

Recently, targeted cancer therapies emerge to direct at the molecular pathways that underlie the malignant phenotype. These therapies target specific tumor cell receptors or signaling events that are critical to tumor progression while reducing toxicity to normal cells.

One limiting factor for targeted cancer therapy is to identify the right tool and monitor its effect on tumor suppression. For example, for most cancers that have metastasized it is urgent to have early effective diagnostic tools, so that physicians are able to replace ineffective therapies with potentially more effective therapies. The selection of the appropriate therapy remains a difficult decision for physicians. To accurately assess the effect of any cancer treatment, reliable device and method are needed for continuous monitoring of the cancer patient. Therefore, an early and accurate detection method, which facilitates physicians to effectively characterize the cancers and outline the treatment, will save many lives.

This disclosure provides a general tool to effectively select the target cancer patient population, stratify the cancer progression, determine the appropriate cancer therapy, monitor the effect of treatment for personalized cancer diagnostics and therapeutics, and/or identify molecular pathways of any specific malignant phenotype for the discovery of potent pharmaceuticals.

SUMMARY

This disclosure reveals a portable device for targeted cell separation and enumeration and its broad use in detecting circulating tumor cells (CTCs). CTCs can be utilized to evaluate the drug effect of cancer treatment, predict the metastatic progression, and screen possible drugs targeted to disrupt malignance related phenotype.

The disclosed device is comprised of two layers, one lid and one base, connected by a one way turning button. The body of the lid comprises an opening through the lid, and a sliding inspection window above the opening on the lid's top surface. In one of the embodiments, a test strip membrane is embedded in the opening via an appropriate flow-through support. The base contains multiple independent rooms that are sized to hold at least the lid's opening (and the test strip). The lid and the base are configured that when the lid is on the open position, the spring inside the turning button is pressed to separate multiple protuberances built on the base away from the corresponding cuts on the lid. When a one way turn is made at the open position, the lid opening along with the test strip inside is moved into the next independent room for reaction needed in that particular stop. Depending on the particular step of cell separation and enumeration process, the independent room may contain absorbent material, an incubation cell for specific binding reaction, or a glass slide for optical observation under the microscope.

In one of the embodiments, the strip is configured to enrich targeted cell type by its pore size.

In yet another embodiment, the strip is configured to have at least one segregated positive control area and at least one working area.

This disclosure also reveals a method of using the disclosed portable device to separate target circulating tumor cells (CTCs) that display a metastatic specific biomarker and to enumerate them under a microscope. A properly treated blood sample is applied to the test strip in the lid's opening to enrich the target cells. Subsequently, the following steps are carried out in each independent room of the portable device: washing, incubation with a specific binding moiety to target cell surface biomarker, and optional enhancement of the specific binding to facilitate the optical observation/enumeration of the target CTCs. By turning the button one way during the operation, the disclosed device carries the test strip with enriched CTCs into each of its intact destination rooms sequentially, eliminating the possibility of cross contamination by different reagents. Each destination room may contain absorbent material, an incubation cell or glass slide, depending on the specific function of that room. The properly stained CTCs are enumerated under optical microscopy directly from the disclosed portable device's last independent room.

One embodiment of the disclosed method is to separate and enumerate CTCs that over express integrin $\alpha v \beta 3$.

One embodiment of the method is to separate and enumerate CTCs that express cytokeratins.

These and other features, aspects and advantages of the present invention will become better understood with reference to the following drawings, description and claims.

BRIEF DESCRIPTION OF FIGURES

FIG. 1 45° top-view of the device after assembly: (11) lid; (12) base; (13) one-way turning button; (14) sliding cover with an inspection window; (15) glass imbedded in the inspection window; (16) opening in the lid; (17) strip membrane imbedded on the bottom surface of the lid opening.

FIG. 2 45° top-view of the device before assembly: (11) lid; (12) base; (13) one-way turning button; (14) sliding cover with an inspection window; (15) glass imbedded in the inspection window; (16) opening in the lid; (17) strip membrane imbedded on the bottom surface of the lid opening; (18) mesh immobilized on the bottom of the lid opening to mechanically support the abovementioned strip membrane; (19) screw cap; (20) spring; (21) cut on the edge of the lid; (22) protuberance on the edge of the base; (23) room 1; (24) room 2; (25) room 3; (26) room 4; (27) room 5; (28) room 6; (29) room 7; (30) absorbent materials; (31) glass slide.

FIG. 3 45° bottom-view of the device before assembly: (11) lid; (12) base; (18) mesh immobilized on the bottom of the lid opening to mechanically support the abovementioned strip membrane; (19) screw cap; (31) glass slide; (32) suction cup.

DETAILED DESCRIPTION OF PREFERRED EMBODIMENT

Figure 1:
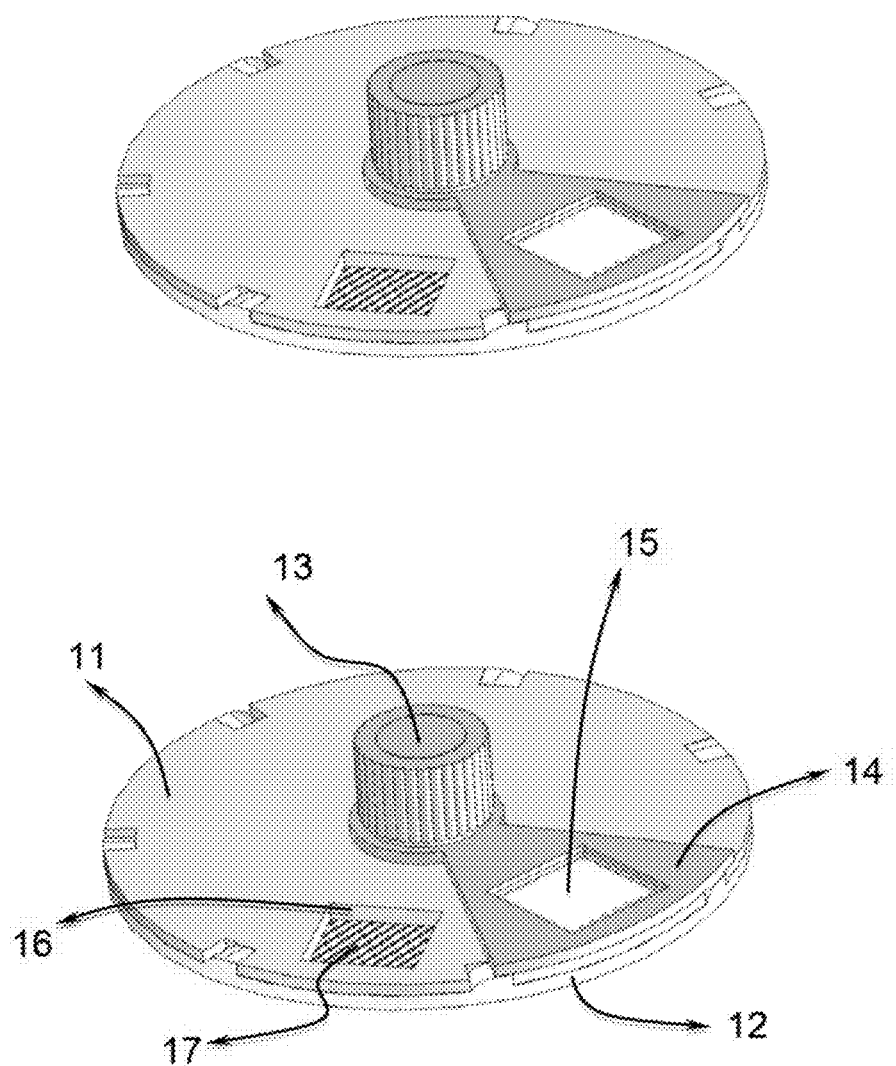

While the concepts of the present disclosure are illustrated and described in detail in the drawings and the description herein, such an illustration and description are to be considered as exemplary and not restrictive in character, it being understood that only the illustrative embodiments are shown and described and that all changes and modifications that come within the spirit of the disclosure are desired to be protected.

Cancer cells are known to mutate, rendering primary tumor limited value for therapy guidance. With increasing knowledge on metastatic cancer, physicians have identified several molecules that have played important roles in tumor metastasis. Accordingly, treatment options are increasing for cancer patients with the introduction of new cancer drugs that disrupt those key molecules in tumor progression and various combinations of existing cancer drugs.

For example, the notion that tumor angiogenesis may have therapeutic implications in the control of tumor growth was first introduced by Dr. Judah Folkman in 1971. The approval of AVASTIN® (Bevacizumab, Genentech/Roche) in 2004 as the first antiangiogenic systemic drug to treat cancer patients came as a validation of this visionary concept and further boosted the quest for new therapeutic targets and antiangiogenic drugs. Vascular integrins have demonstrated the potential by preclinical and clinical studies. Representative biological drugs which target integrin αvβ3 are Etaracizumab (VATAXIN®, MedImmune Inc., Gaithersburg, Md.; phase II clinical trial in New York, US), Cilengitide (Merck KGaA, Darmstadt, Germany; phase II and III clinical trials in Europe, Canada and US), and S247 (Pfizer, St Louis, Mo.).

In the meantime, because most chemotherapy drugs are toxic with undesirable side effects, the balance between widely accepted chemotherapies and immature target therapies such as antiangiogenic therapy with fewer side effects becomes critical. Therefore, a diagnostic tool that aids doctors' therapy selection would improve the efficiency in cancer treatment, which may eventually reduce the overall medical cost and extend the patients' lifetime.

Cancer imaging has been broadly used to localize the tumor and monitor the tumor progression, especially metastatic cancers. However, cancer imaging has limitation in application with its conservative sensitivity and specificity. For example, mammography is highly accurate in breast cancer detection, but only identifies 80-90% of the breast cancers in women without symptoms. The reason for missing identification could be because of high breast density at young age, poor positioning of the breast, or low sensitivity in recognizing small breast tumor at early stage. MRI (Magnetic resonance imaging) is another major imaging tool for breast cancer screening by finding very small tumors and tumors in very dense breasts. MRI also finds more tumors than mammography. However, MRI is not perfect, either. It is expensive, costing approximately $1,000 compared to $100 for a mammography in average. Although MRI finds more cancers, it will not find them all and also provide false positive reading, which leads to twice as many unneeded additional examinations as mammography and three times as many unnecessary biopsies. In addition, inconsistent MRI interpretation often occurs at different sites by different radiologists. Furthermore, MRI cannot be a routine test readily available for constantly monitoring tumor progression and metastasis.

Serum tumor biomarkers are released to the blood stream by the tumors, possessing direct information about the current status of the tumors. For an instance, serum carcinoembryonic antigen (CEA) is an extensively examined biomarker for lung cancers and found elevated especially in adenocarcinoma and large cell lung cancers. CEA, however, is expressed in non-tumor cells as well and associated with cancers other than lung cancer. Due to its poor sensitivity, specificity and reproducibility, CEA has not been recommended for clinical diagnostics in practice. To date none of the serum tumor biomarkers have been proven exclusive for a specific tumor. The level of these biomarkers could vary in the range that cancer patients cannot be accurately separated from normal people. Additionally, during cancer treatment cancer patients may not demonstrate elevated concentration of these biomarkers. Therefore, quantitative measurement of serum tumor biomarkers alone lacks the specificity in cancer diagnosis and prognosis.

Metastatic tumors or even the primary tumors without metastasis shed off tumor cells which travel through the circulation system (Circulating tumor cells; CTCs) and lodge to a distant organ resulting in angiogenesis and metastasis. CTC levels have been closely related to the metastasis and poor prognosis such as in lung, breast, colon, esophageal, and prostate cancers. It is therefore an increasing held view that CTCs are a vital stage in the metastatic cascade, and have a clinical significance to early cancer diagnosis, prognosis and monitoring of cancer progression, assessment of tumor reactivity to anti-cancer drugs, and personalization of cancer therapies. The detection of CTCs thereafter becomes a unique method to identify metastatic cancers earlier, less invasively and more reliably than the conventional means, such as clinical exams, radiographic imaging and serum tumor biomarkers do.

In 1869, Ashworth first described the presence of tumor-like cells in the peripheral blood from a cancer patient by autopsy. Ashworth's observations generated many interests in revealing mechanisms of metastasis and tumor cell dissemination. Paget, in 1889, was the first to hypothesize a nonrandom pattern of distant tumorigenesis and, as a result, developed the "seed and soil" theory of cancer metastasis that certain subpopulations of tumor cells travel through systemic circulation as seed and metastasize to selective organs with similar characteristics. Accumulating evidence has suggested that localized tumors begin shedding CTCs during early stages of the disease, with distinct cell populations having the potential to develop into metastatic disease.

With the advance in technology in latest 1-2 decades, the value of CTCs as diagnostic, prognostic and predictive markers for cancer metastasis has been highly appreciated. In 1998, Racila and his co-workers first quantified the CTCs for breast cancer using multiparameter flow cytometry. Peripheral bloods from 30 patients with breast carcinoma as well as 13 healthy donors were examined. In the control group, the average number of epithelial cells ranged from 0-5. In contrast, there were an average of 15.9±17.4 epithelial cells per sample for the patients with localized breast cancer, 47.4±52.3 cells for those with only lymph node spread, and 122±140 in patients with distant metastasis.

Flow cytometry is a technique widely used in cell biology and clinical diagnostics. However, it has its own limitations. Most notably, the technique requires frequent calibration, specially trained personnel to maintain the expensive equipment, and highly skilled professionals to perform data acquisition and analysis. The fact that there are two major Flow Cytometry machinery manufacturers often raises data incompatibility issue. Because of the rare existence of CTCs in the early metastatic blood samples, flow cytometry represents a technique that has low sensitivity and poor reproducibility to achieve the goal of early diagnosis.

Another important technique to acquire the number of CTCs in blood samples from healthy subjects, patients with nonmalignant disease, and a variety of metastatic carcinomas is semi-automated CellSearch system. CellSearch system utilizes ferroparticles (namely magnetic particles) coupled EpCAM antibody to separate CTCs. Enriched CTCs are then labeled with fluorescent antibodies to intracellular cytokeratins, fluorescent nuclear dye DAPI, and a fluorescent antibody to CD45 specific to leukocytes. Labeled CTCs are next identified by the CellTrack Analyzer II for positive cytokeratin staining, negative CD45 staining, and a clear DAPI positive nucleus.

Using the CellSearch system, in 2004, Cristofanilli and his team conducted a multicenter clinical study for 177 patients with metastatic breast cancer in determining the correlation between the levels of CTCs and the progression-free and overall survivals. The results elucidated that 5 CTCs per 7.5 mL of blood can be chosen as a cut-off to distinguish patients with poor prognosis from patients with favorable prognosis. Studies also exhibited the levels for healthy women and patients with benign breast tumor with means of 0.1±0.2 and 0.1±0.9 per 7.5 mL of blood, respectively. Based on the statistical study, the number of CTCs is demonstrated an independent predictor for disease progression and survival in metastatic breast cancer and a therapy-guiding indicator for patients before and after the initiation of therapy.

In 2009, Tanaka et al. investigated the diagnostic performance of CTCs in patients with a suspicion or a diagnosis of primary lung cancer using CellSearch System. Of 150 eligible patients, CTCs were identified in 31% of lung cancer patients and 12% of nonmalignant patients. CTC levels were significantly higher in lung cancer patients than those in nonmalignant patients. Among lung cancer patients, the number of CTCs significantly increased with tumor progression, especially after distant metastasis. If patients with ≥1 CTCs were stratified as having metastatic disease, sensitivity and specificity of the CTC test were 71% and 83%, respectively. Therefore, CTC is a valuable surrogate marker of distant metastasis in primary lung cancer.

Detection of CTCs can also be used in conjunction with the drug effect evaluation. For example, in US Patent Application Publication 20090117532, Doyle disclosed a "Pre Clinical Method for Monitoring Serial Changes in Circulating Breast Cancer Cells in Mice." The system used by Doyle is a Cell-Track Analyzer to enumerate enriched breast cancer cells. Similarly, in US Patent Application Publication 20090136946, Connelly et al. disclosed a method for automatic enumeration and characterization of circulating melanoma cells in blood. The automatic system disclosed in these two patent applications (both belonging to Johnsons & Johnsons) demonstrates the need of repetitively monitoring serum CTCs to achieve the goal of drug effect evaluation. Essentially, an effective drug treatment on metastatic cancer would result less targeted CTCs in blood. By continuously monitoring the CTC levels in blood, physicians and researchers can assess the efficacy of any drug treatment, and make informed decision whether to continue the elected drug treatment, at the backdrop of the overall patient tolerance to the treatment, such as the side effects, etc. The US Patent Application Publications of 20090117532 and 20090136946 are incorporated herein to demonstrate the need for easy and routine serum CTC level monitoring to evaluate drug's efficacy. The system disclosed in these two applications, however, is not suitable to achieve such frequent monitoring purpose, due to the high cost and complexity of the maneuver. Hence, an easy and simple system without impairing the sensitivity and reliability is highly demanded.

More broadly, if a particular metastasis malignance phenotype CTC is known, a sensitive and reliable CTC detection system can be used to perform targeted drug screening. In essence, any drug that disrupts the known malignant CTC phenotype can be identified as a positive candidate. In US Patent Application Publication 20080318324, Chiu et al. disclosed a biochip for high throughput screening of CTCs. The system provides a one dimensional channel to isolate/enrich CTCs by filtration. In US Patent Application 20090035792, Singh et al. disclosed the compositions and methods for detecting the activation state of components of signal transduction pathways in tumor cells. These two application publications are incorporated herein to demonstrate the basic principle of mass screening to identify possible drugs effective on tumor cells, i.e., to interpret any drug treatment resulting signaling molecule fluctuation in isolated CTCs, and hence inferring the efficacy of the drug induced CTC reduction. However, neither of them is designed for targeted CTC total cell assay in patient samples to assess the candidate drug. The complexity of one dimensional filtration flow channel is not suited for convenient handling of CTC enrichment, whereas the drug screening composition and method disclosed in 20090035792 requires CTC cell extract analysis to indirectly determine the drug effect on CTC reduction in blood sample. In the process of cell extract analysis, CTC loss is unavoidable, rendering the result less reliable compared to direct CTC assessment. What is needed for drug screening purpose is a single portable device that is capable of enriching targeted CTCs with simple steps, easy operation and direct drug analysis.

Successful early detection of CTCs relies on well-established molecular biomarker on CTCs to serve its important roles in cancer diagnosis, drug screening, drug efficacy evaluation, and therapy guidance. This disclosure provides a tool to use CTC surface biomarkers, such as integrin $\alpha v \beta 3$, to detect metastatic tumor cells in the circulating system. Integrin $\alpha v \beta 3$ is a transmembrane adhesion receptor that facilitates tumor cells to adhere to the extracellular matrix, the adjacent cells, and the distance organs and metastasize. Integrin αvβ3 plays a major role in various cancer stages, such as tumor growth, progression, invasion and metastasis, and has been implicated in the pathophysiology and progression of several malignant tumors, such as melanoma, glioma, ovarian, prostate and breast cancer. In breast cancer, integrin αvβ3 has been found associated with high malignant potential in cancer cells, signaling the onset of widespread metastasis. Importantly, integrin αvβ3 expresses at low levels on mature endothelial cells and normal organs. The highly restricted expression of integrin αvβ3 in normal tissues and overexpression on tumor cells presents an interesting molecular biomarker for early cancer detection.

Despite optimization of surgery, radiation therapy and cytotoxic chemotherapy, overall survival of advanced cancers is poor. A promising solution is to select personalized cancer diagnostics and therapeutics. However, personalized medicine depends on individualized targets. The biomarker on CTCs, which embody the fingerprint of the metastatic cancer from individual patient, could be the most potent target that ever explored. By disrupting the specific biomarker on CTCs cancer therapy is personalized. For example, the inhibition of the over-expressed integrin αvβ3 receptors on CTCs could be one of the personalized anti-angiogenesis therapies. VITAXIN® (Etaracizumab, MedImmune Inc) is an anti-αvβ3 antibody that currently undergoes phase II clinical trials. It has demonstrated potential as a αvβ3 inhibition therapy in treating colon, kidney, lung, breast, and prostate cancers. Some patients, if confirmed as αvβ3 positive in CTC detection, could have responded to this therapy using VITAXIN® more significantly than others who are αvβ3 negative, because αvβ3 inhibition therapy gives a synergistic effect by blocking or inhibiting both angiogenesis and tumor cells including CTCs. CTC detection of integrin αvβ3 will be, therefore, an effective, safe, easy and promising strategy to guide personalized anti-angiogenesis therapy for clinical practice.

Studies have established the correlation of biomarker bearing CTCs with the prognosis of tumor metastasis, i.e., the number of CTCs before treatment is an independent predictor of progression-free survival and overall survival in patients with metastatic cancer. In addition, if a biomarker, such as αvβ3, is established to have positive correlation with malignant metastatic tumor cells, effort of disputing such biomarker or its related signaling events can lead to the inhibition of metastasis. As a result, drug screening using CTC level as an efficacy read out is an easy and efficient way to discover new therapy for a known malignancy phenotype.

Physicians and researchers attempted to use various techniques to achieve early analysis of such biomarker bearing CTCs in the patient blood. However, the available techniques are not sufficient. For example, in U.S. Pat. No. 5,648,223 to Peter Van Vlasselaer, the inventor used centrifugation and gradient specific cell trap to enrich circulating breast tumor cells in patient's body fluid. The enriched breast tumor cells can be subsequently confirmed by molecular or immunochemical means, or purged from an autologous bone marrow transplant prior to reinfusion. The devices and methods used in these studies require sophisticated machines, such as flow cytometer, CellSearch workstation and fluorescence microscope, centrifuges, etc. The complexity and cost of these machineries prevent end users, such as laboratories/clinics to accurately and promptly detect CTCs with ease. A critical issue in the use of the CellSearch system is its low sensitivity in detecting CTCs. Other techniques incorporated herein do not resolve the challenge presented in continuous monitoring of CTC level of patients in near-real time. For a comprehensive review of current available technologies for detecting CTCs, see Bianca et al. Cancer Treatment Reviews, 35 (2009), 463-474.

To properly isolate/enrich the tumor cells such as CTCs in a given body fluid, and accurately detect the tumor cell levels without cell loss, a more sensitive and easy detection system is in need of the field. This disclosure and some of the embodiments illustrate how to solve these problems.

CTC Identification By Size and Specific Tumor Marker. Red blood cells (RBCs), white blood cells (WBCs) and platelets are the three major cells in the whole blood. For CTC detection, reduction and exclusion of the effect of these cells is crucial. RBCs, the most abundant cells in blood (about 80-90% of the total cells), are easy to remove by commercially available hemolytic method. Therefore, WBCs and platelets will be the main cells left in the detection sample. The sizes of these cells are distinctly different. Most WBCs are between 10-15 μm; platelets are about 2-3 μm in diameter; while CTCs are normally larger than 30 μm. Due to the cell size difference, platelets could be distinguishable under microscope. Therefore, the specific biomarkers for CTCs, without binding of WBCs, for example, but not limited to integrin αvβ3, would be appropriate for the detection of CTCs in addition to size difference.

Blood Separation and Cell Enrichment by Strip Membrane using Flow-Through Paper Filtration Technology. Blood cells can be separated from plasma by membrane with accurately controlled pore sizes. Cell based immunoassay can be also performed on membrane when the membrane acts as a cell pad where it captures cells, disposes of the blood residue such as proteins and erythrocyte lysate, accepts the reagents/conjugates/wash-buffer and performs flow-through assay. Strip membranes are commercially available to provide: (1) Single unit for blood separation and flow-through assay; (2) Natural hydrophilicity and no need for blocking; (3) High test sensitivity and low background due to non-protein/conjugate binding characteristics; (4) High resistance to solvents, amides and halogenated hydrocarbons; (5) High reliability and easy QC for using single materials; (6) Easy and efficient manufacturing helpful in speeding products to market.

A portable device for the separation and detection of whole CTCs from other blood cells in patient samples is designed, and the enumeration of such CTCs on the device is achieved by simple steps.

In one embodiment, flow-through paper filtration technology is used in a single portable device to determine whether a patient's blood sample contains the level of CTCs to cause physician therapy alertness, for example, to evaluate whether any drug treatment has achieved its targeted effect (i.e., reduce the level of biomarker bearing, metastatic, malignant CTCs), or to mass screen drug candidates for targeting specific malignance phenotype. The device is manually operated by an end user. Briefly, the device contains two separate bodies, a lid and a base, and the two are separable by pressing a spring connected in a one way turning button. The lid and the base are configured to have multiple matching protuberances and cuts to accommodate the closed position in a given turning stop. At the bottom surface of the lid, an opening is included to accommodate a test strip fixed thereon to receive blood sample or other body fluid of interest. The test strip membrane is made to capture the cells of interest, either by its size preclusion, or other physical features unique to the targeted cell for separation. Above the opening, a removable cover with an inspection window is made on the top surface of the lid to provide protection and observation of the opening when needed. The base has at least two, if not more independent rooms that are sized at least to hold the opening/test strip therein.

In the initial position, the test strip is resting in the first independent room of the base. Samples are added to the test strip through the lid opening to capture the targeted cell population. Depending on the cell separation protocol and the illumination method involved in the subsequent steps, the independent rooms at the base may contain absorbing material, incubation room or only a glass slide for viewing the captured/stained cells on the test strip membrane.

For example, one embodiment could be the test membrane separating target cells, in this case CTCs, from other blood cells by its membrane pore size. Such membranes are commercially available or easy to design according to the needs. In US Patent Application Publication 20060254972, Tai et al. disclosed membrane filter for capturing circulating tumor cells. Basically such membrane filter has an array of holes having a predetermined geometric design with precisely controlled size, shape and density. US 20060254972 is incorporated herein to demonstrate the skill of art in pore size based cell exclusion in membrane design.

If the targeted cells for separation, in this case, CTCs, have a marker that is specifically expressed on the cell surface, the separation and enumeration of the targeted cells can be based on such over-expressed surface marker. For example, the test strip could first allow non-size-compliant blood cells to flow through. Subsequently, the test strip with the captured cells are incubated with CTC-specific binding moieties to the marker, and examined by routine optical microscopy according to the binding/staining protocol adopted in the process. Because the device has multiple independent rooms to accommodate the skill of art immunocytochemistry protocol or other standard detection means, the device provides a one stop shop of targeted cell separation and enumeration.

Alternatively, the test strip may contain specific binding moiety to the targeted cell surface marker, for example, in the case the metastatic specific adhesion molecule on CTCs. The test strip itself may be designed not only to perform cell exclusion function, but also contains adhesion molecule specific binding moiety, such as antibody or short synthesized peptides, etc. This way when the sample is applied to the membrane, the CTC capture is more specific because of the pore design and the binding of the moiety.

The use of the device involves multiple steps of lifting the one way turning button to separate the lid and the base, and turning the button one way to move the test strip into the next independent room to perform the next function of the separation and enumeration. For example, after the sample is applied to the test strip and non compliant cells as well as plasma flow through the membrane, or the targeted cells are specifically bound by moiety embedded/immobilized on the test strip, the test strip may be moved to the next room which contains absorbent material for washing step. Or the test strip might need to be incubated for enhancing the viewing of the specific binding, for example, metal substrate for the binding moiety that is observable under regular optical microscopy.

The statistics of how to interpret captured CTCs' reading, compared to positive controls or pre-treatment data, are common to people skill in the art, and will not be described in detail. See Cristofanilli et al. (2004).

Although the device is exampled to be used in CTC counting from a patient sample for the applications in cancer diagnosis, prognosis and cancer drug discovery for physicians or researchers, the principle of the device can be used in various other disciplines. For example, with protocol modification, the device can be used for target cell lysate analysis. Replacing the whole blood sample with cell lysate and fine tuning the membrane strip may render the device capable of identifying targeted protein/enzyme in a given cell lysate.

Further, if the device is designed by automatic maneuver for multiple assays, with proper enumeration software available in the art, it could become an efficient screening device for multiple drugs.

Example 1

A Portable Targeted Cell Separation and Enumeration Device

One embodiment is a disposable point-of-care in-vitro assay device specially designed to provide guidance for integrin αvβ3 inhibition therapy, in accordance with the urgent request on anti-angiogenic drugs targeting integrin and the huge market for cancer care. The device can be utilized in-house to easily visualize and count the circulating tumor cells in the blood stream of the cancer patients in 40 minutes. The number of circulating tumor cells has been found closely related to cancer staging, metastasis, progression and overall survival rate, and therefore, is increasingly important in selecting the target patient population, stratifying the cancer progression, determining the treatment plan, monitoring the therapeutic efficacy, and eventually personalizing the cancer therapy regimen.

Figure 2:
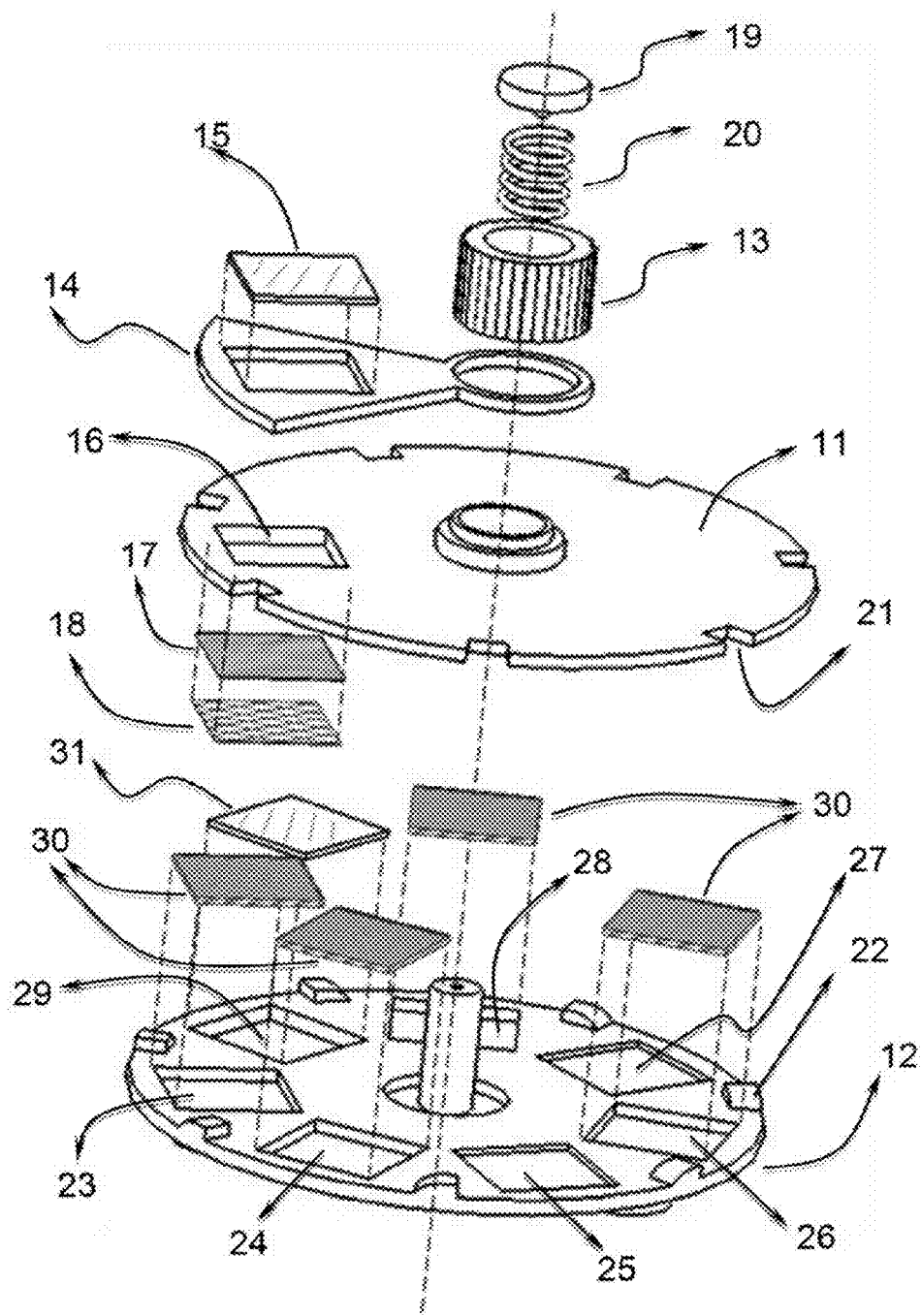
Figure 3:
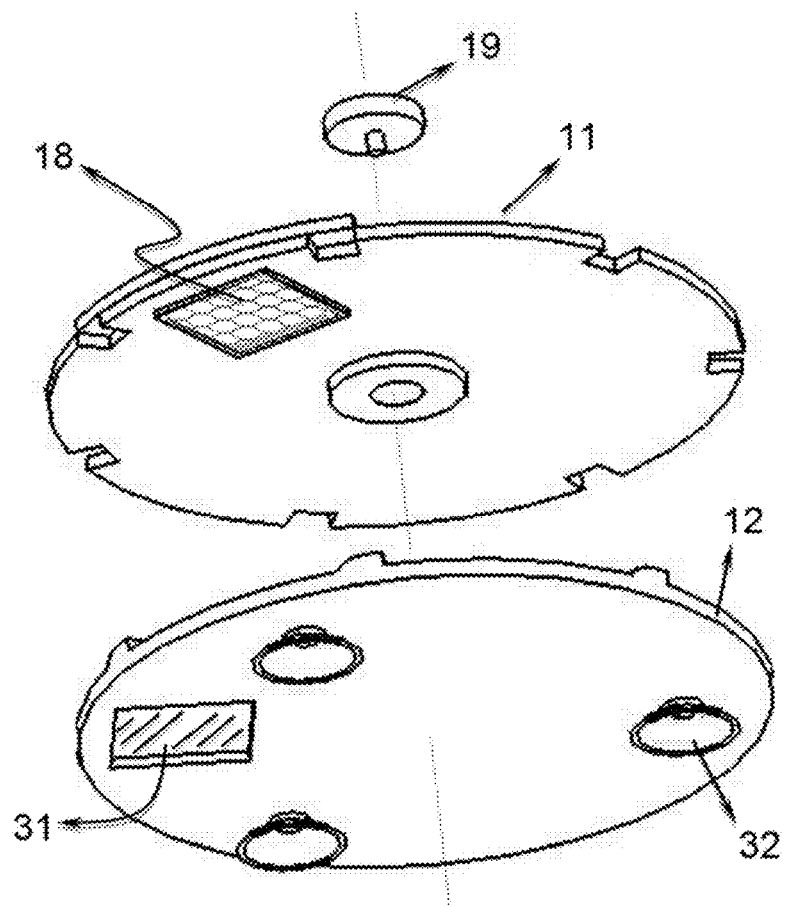

The cell separation and enumeration assay device, shown in FIG. 1-3, works manually and cost-effectively, requiring no technical background for operation and no centrifuge for blood sample treatment as highly required by conventional blood cell analysis. The device contains two plastic layers: the lid (11) and the base (12). On the lid, there are a turning button (13) for rotating the lid, a sliding-cover (14) with inspection-window (15) for protecting the lid opening during incubation and for reaction inspection, a lid opening (16) containing a fixed strip membrane (17) on a mesh (18), a screw cap (19) for fixing the turning-button on the lid, a spring (20) which can be pressed to separate the lid from the base, and 7 cuts (21) for fixing the position of the lid on the base. On the base, there are 7 protuberances (22) to match the cuts on the lid and 7 reaction rooms (23-29). From Room 1 to Room 7, they represent 7 steps of the cell assay which is stated later. Room 1 (23), 2 (24), 4 (26) and 6 (28) have the absorbent materials (30) in the room for absorbing blood residue, waste of reagents and wash solution. Room 3 (25) and 5 (27) provide the incubation well for conjugate and metal staining reactions, respectively. Room 7 (29) contains nothing but a glass slide embedded (31). The device looks like a disc after assembled and fastened by a spring (20). The rotation of the lid over the base from one room to the next is achieved by lifting the lid above the protuberances (22) and counterclockwise rotating the lid to let the cuts (21) fit to next protuberances. Three suction cups (32) are attached to the bottom surface of the base to immobilize the device during operation.

When a blood sample arrives, it is mixed with red blood cell lysis buffer within two hours of blood withdraw to eliminate the interference of dominant red blood cells. The lysate is then added to the device through the lid opening.

Figure 4:
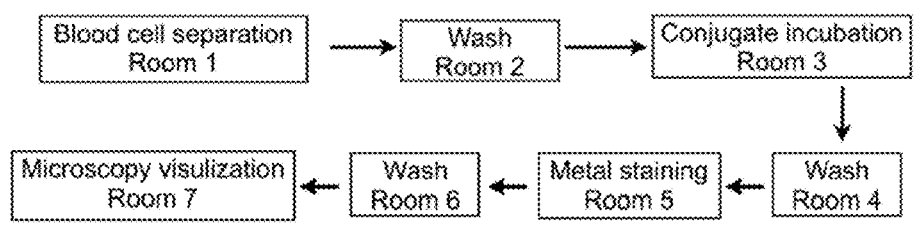
FIG. 4 Flow chart for the flow-through cell assay on the test strip in device.

There are totally seven steps in completing a flow-through cell separation and enumeration assay (FIG. 4) on the strip membrane, with each step assigned by a stop during the one-way rotation of the device. At each stop, either cell wash or incubation reaction is achieved in an isolated room, simplifying the testing procedures for the end-users. The one-way rotation and isolated rooms prevent the possible cross-contamination between steps. The design also realizes the static incubation during flow-through assay on strip membrane by incorporating an incubation cell. At the last step of the assay in Room 7 (29), the strip membrane in the device with stained circulating tumor cells on the surface is examined under an ordinary light microscope. The independency from sophisticated technology and equipment increases the reliability and reproducibility of the testing and reduces the diagnostic cost. Another competitive advantage of this flow-through cell separation and enumeration device is that cell-loss-free can be fulfilled by tightly controlled pore size of the strip membrane as well as no centrifuge or other physical manipulations involved.

The cell assay completes in Room 6 (28) and then the strip membrane is relocated to Room 7 (29), sitting on the glass slide. Next, the entire device will be moved under the light microscope with Room 7 (29) right below the objective lens for cell imaging.

Assay Protocol
Pre-Assay Blood Treatment

Blood collection: 7.5 mL of blood is collected into heparin/EDTA/Citrate containing tube from cancer patient. Two specimens are collected from each subject, with 2.5 mL of blood in the first tube and 5.0 mL in the second tube. The first tube, which may be contaminated with the epithelial cells picked up by the needle, is then discarded, and only the second tube is used. Within 2 hr after being drawn, blood is processed in a designated blood-processing laminar hood.

Red Blood Cell Lysis: Since a majority of blood cells are red blood cells, the lysis step concentrates the CTCs and eliminates the background red color to facilitate CTC chromogenic analysis. Red blood cell (RBC) lysis buffer, which is designed for the optimal removal of RBC with none-to-negligible effect on CTCs and white blood cells, is selected and used according to the manufacturer's instructions. Briefly, 5.0 ml of RBC lysis buffer is added to 5.0 ml of whole blood. After inverting the tube to mix the solution and incubating for 10 min at room temperature, sample is ready for cell assay.

Cell Assay in Device

Figure 5:
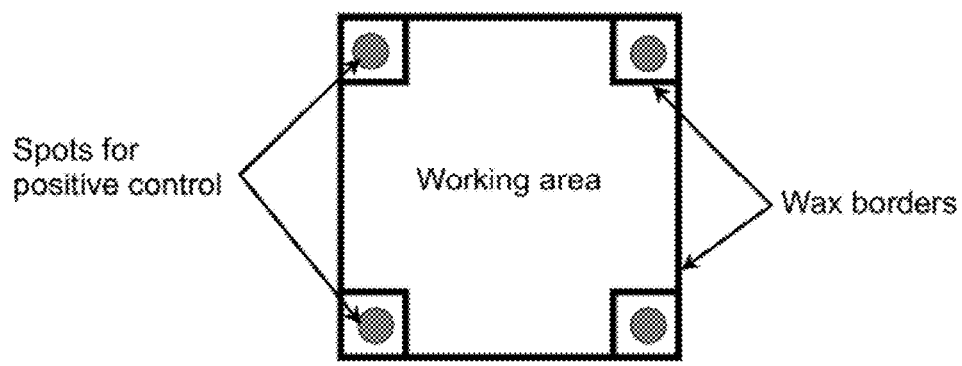
FIG. 5 The diagram for the top view of a test strip with working area for blood cells in the center and positive control beads located on the four corners, separated by the wax lines.

Step 1—Blood Cell Separation in Room 1 (23): The treated blood specimen (10 mL) is poured onto the working area (FIG. 5) of the strip membrane (17) through the opening (16) on the lid (11). Since the membrane is in contact with the absorbent materials (30) in Room 1 (23) through the mesh (18), which holds the membrane in the opening of the lid, proteins and erythrocyte lysate in the blood specimen will flow through the membrane and are absorbed by the underlying absorbent materials. White blood cells and CTCs are thus enriched on membrane.

Step 2—Rinsing of Blood Cells in Room 2 (24): The strip membrane is lifted with the lid and rotated to Room 2 (24) with fresh absorbent materials. The wash buffer is pipetted to the membrane to rinse the blood cells and remove the proteins and other blood residues.

Step 3—Cell Incubation with HRP Linked Anti-Human Integrin αvβ3 Conjugate in Room 3 (25): The strip membrane is lifted with the lid and rotated to Room 3 (25) with an incubation cell/well. The anti-human integrin αvβ3 conjugate is then pipetted onto the membrane to fully wet it. The incubation takes 15 minutes.

Step 4—Cell Washing in Room 4 (26): Similar to step 2, the membrane is relocated to room 4 (26) with fresh absorbent materials. Wash buffer is applied to wash out the unbound molecules from cells.

Step 5—Cell Staining by Metal Substrate in Room 5 (27): The membrane on the lid is lifted and transferred to Room 5 (27) with incubation cell/well. The freshly prepared metal substrate is pipetted onto the membrane to fully wet it. The metal precipitation on cell surface is allowed for 10 minutes.

Step 6—Cell Washing in Room 6 (28): Same as step 4 to remove the residue of the metal substrate.

Figure 7:
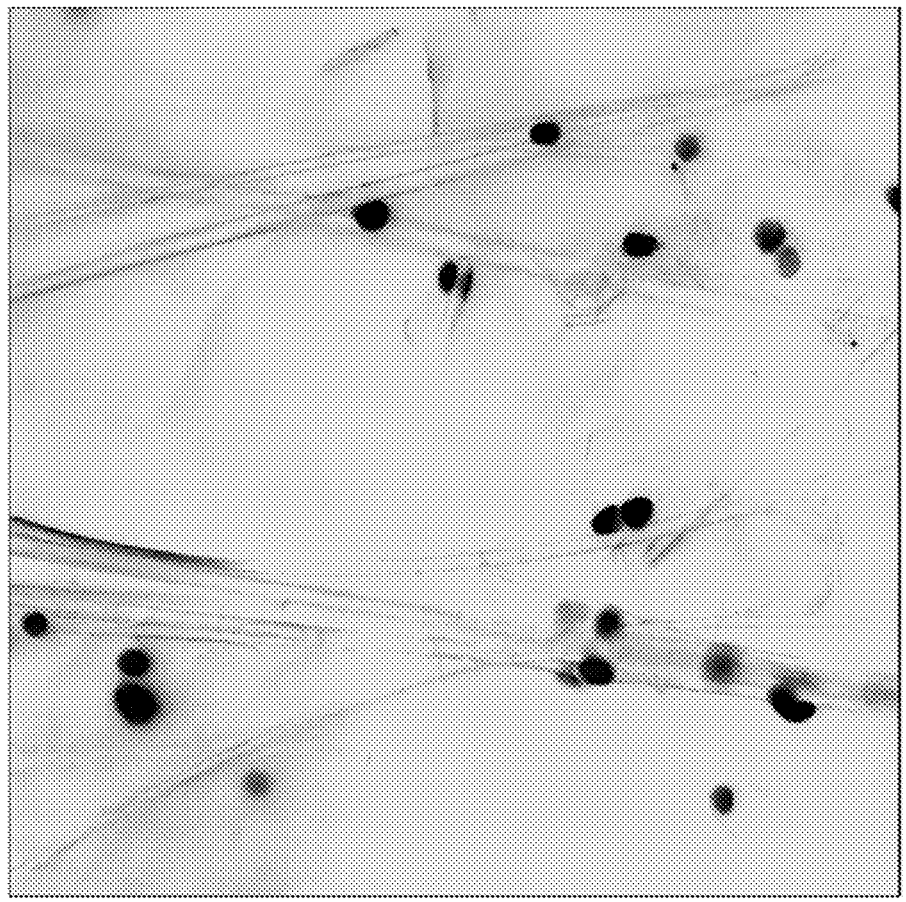
FIG. 7 MDA-MB-435 human breast cancer cells on the strip membrane after staining of cytokeratin with metal precipitation (dark blots), magnification 20×. Some paper fibers were also shown.

Step 7—Cell Visualization in Room 7 (29) under light microscope: After the washing in step 6, the membrane is removed to Room 7 (29) to sit on a glass slide (31). The entire device is then moved under a light microscope for cell inspection. At 20× and up magnification, metal stained CTCs are shown as dots with dark color (FIG. 7). The number of the CTCs is then counted. The CTCs are available for further analysis. The automatic CTC enumeration can be achieved by computer aided imaging.

The entire assay time is expected to be around 40 minutes.

Example 2

Figure 6:
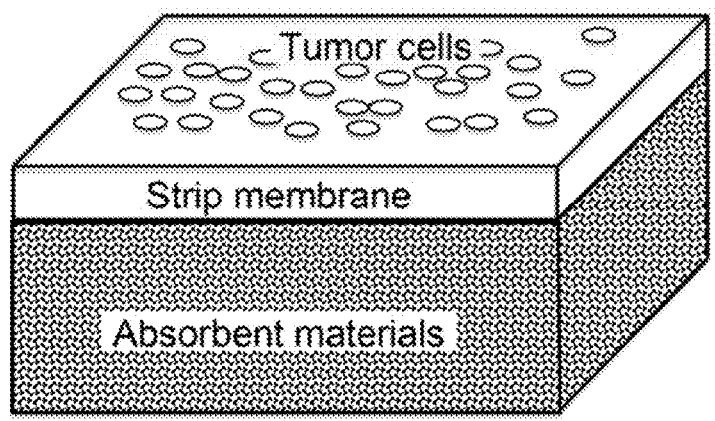
FIG. 6 Construction for a flow-through assay with a strip membrane layer and the underlying absorbent layer. The tumor cells are captured on the surface of the strip membrane.

Tumor Cell Chromogenic Staining on Membrane. Cytokeratins are abundant intracellular proteins expressed by most types of carcinoma, and therefore, are one of the most widely used CTC biomarkers for CTC identification. To explore the feasibility of metal enhanced detection and enumeration of CTCs, cytokeratins were targeted and stained by metal to recognize the tumor cells. Culture tumor cells were used to mimic isolated CTCs. The staining experiment was conducted directly on the culture tumor cells placed on the test strip (i.e., strip membrane). Human breast cancer MDA-MB-435 cells were first cultured, trypsinized and washed. After resuspended in buffer in the microcentrifuge vial, MDA-MB-435 cells were reacted with mouse anti-human cytokeratin 8, 18 and 19 for 60 min and followed by HRP-linked anti-mouse antibody (dilution: 1:100) for another 60 min. Approximately 1,000 cells, which were washed after reactions, re-suspended in 0.5 mL of PBS buffer and counted using hemacytometer, were evenly distributed onto an 1×1 cm strip membrane. There was an absorbent pad under the strip membrane (FIG. 6). The cells were further rinsed twice with deionized water.

To prevent dust contamination, cell washing and staining were performed in the laminar hood. Wash buffer went through the test strip and was absorbed by the underlying absorbent. Then the semi-dried strip membrane was relocated to a cell culture dish without the underlying absorbent. Freshly prepared 1× metal substrate solution was added to fully wet the membrane; the dish was then sealed with the petri-dish cover; and the incubation was 10 minutes. Next, the membrane was removed, sitting on a new absorbent pad, and washed twice with deionized water. The semi-dried membrane was then examined under microscope (20×). As shown in FIG. 7, MDA-MB-435 breast cancer cells were stained in black, enabling clear observation.

It should be understood, of course, that the foregoing relates to exemplary embodiments of the disclosure and that modifications may be made without departing from the spirit and scope of the invention as set forth in the following claims.

The invention claimed is:

1. A portable device for targeted cell separation and enumeration, comprising:
    a lid, wherein the center of said lid contains a hollowed one-way turning button with at least two stops, the edge of said lid is configured with at least two cuts, and the body of said lid comprises
        a single opening, wherein a strip membrane is supported on said opening through an appropriate flow-through structure; wherein said single opening and said strip membrane form a single sample loading area that is permeable through said strip membrane; and wherein said strip membrane is configured by said targeted cell's pore size and collects said targeted cells as retentate;

a base, wherein the center of said base contains a spring projection, the edge of said base is configured with at least two protuberances, wherein said protuberances fit to said cuts, and the body of said base contains at least two independent rooms, wherein each of said independent rooms is sized at least such that said strip membrane can reside entirely inside each said independent room; and wherein, when said cuts and said protuberances are aligned, the said independent room in which said strip membrane resides entirely and said single sample loading area together form said reaction well that is isolated from other said independent rooms;

said lid and said base are configured that said strip membrane can reside inside any of said independent rooms when said cuts and said protuberances are aligned; pressing said spring projection separates said lid and said base; and turning once of said button rotates said lid and carries said single sample loading area with said lid to next said independent room such that said single sample loading area and next said independent room form next said reaction well;

whereby said portable device allows separation and enumeration to be performed in single said portable device by sequentially rotating said single sample loading area to different said independent rooms to form different said reaction wells;

2. The portable device of claim 1, wherein the strip membrane is configured to have at least one segregated positive control area and at least one working area, wherein said positive control area and said working area both are located in said single sample loading area; and wherein same said reaction well carries out same treatment for both said positive control area and said working area simultaneously.

3. A method to separate and enumerate circulating tumor cells (CTCs) and to maintain said CTCs as total cells, wherein said CTCs contain at least one known metastatic specific biomarker, comprising the steps:

a. obtaining appropriate amount of peripheral blood of a cancer patient and properly lysing the red blood cells in the peripheral blood to get a lysate for further analysis;

b. obtaining a portable device, said device comprising:

a lid, wherein the center of said lid contains a hollowed one-way turning button with at least two stops, the edge of said lid is configured with at least two cuts, and the body of said lid comprises a single opening, wherein a strip membrane is supported on said opening through an appropriate flow-through structure; wherein said single opening and said strip membrane form a single sample loading area that is permeable through said strip membrane; and wherein said strip membrane is configured by said targeted cell's pore size and collects said targeted cells as retentate;

a base, wherein the center of said base contains a spring projection, the edge of said base is configured with at least two protuberances, wherein said protuberances fit to said cuts, and the body of said base contains at least two independent rooms, wherein each of said independent rooms is sized at least such that said strip membrane can reside entirely inside each said independent room; and wherein, when said cuts and said protuberances are aligned, the said independent room in which said strip membrane resides entirely and said single sample loading area together form said reaction well that is isolated from other said independent rooms;

said lid and said base are configured that said strip membrane can reside inside any of said independent rooms when said cuts and said protuberances are aligned; pressing said spring projection separates said lid and said base; and turning once of said button rotates said lid and carries said single sample loading area with said lid to next said independent room such that said single sample loading area and next said independent room form next said reaction well;

whereby said portable device allows separation and enumeration to be performed in single said portable device by sequentially rotating said single sample loading area to different said independent rooms to form different said reaction wells;

c. applying said lysate into said strip membrane, wherein the first independent room contains an absorbent material;

d. turning said button for at least once to move said strip membrane into next said independent rooms, wherein at each independent room said strip membrane is sequentially treated with appropriate wash buffer;

incubated with a moiety that specifically binds to said known biomarker on said CTCs; and further incubated with a substrate that specifically illustrates the binding optically;

e. Moving said device under optical microscope and enumerate said CTCs.

4. The method in claim 3, wherein said known biomarker is $\alpha v \beta 3$.

5. The portable device of claim 1, wherein said lid further comprises an inspection window embedded in a sliding cover on said lid's top surface, wherein said inspection window is above said single opening.

6. The portable device of claim 1, wherein said targeted cells are circulating tumor cells.

7. The portable device in claim 1, wherein said independent rooms contain an absorbent material, an incubation cell to hold said strip, or a glass slide.

8. The portable device in claim 1, wherein said independent rooms contain an incubation cell to hold said strip membrane.

9. The portable device in claim 1, wherein said independent rooms contain a glass slide.

* * * * *